United States Patent
Stuebe et al.

(10) Patent No.: US 9,015,615 B2
(45) Date of Patent: Apr. 21, 2015

(54) USER INTERFACE FOR MEDICAL IMAGING SYSTEM APPLICATIONS

(75) Inventors: Susan M. Stuebe, Whitefish Bay, WI (US); Amanda Fox, Fox Point, WI (US)

(73) Assignee: General Electric Company, Schenectady, NY (US)

( * ) Notice: Subject to any disclaimer, the term of this patent is extended or adjusted under 35 U.S.C. 154(b) by 1192 days.

(21) Appl. No.: 12/946,898

(22) Filed: Nov. 16, 2010

(65) Prior Publication Data

US 2012/0124506 A1 May 17, 2012

(51) Int. Cl.
*G06F 3/048* (2013.01)
*A61B 6/00* (2006.01)
*A61B 6/03* (2006.01)
*G06F 19/00* (2011.01)

(52) U.S. Cl.
CPC .......... *A61B 6/463* (2013.01); *A61B 6/032* (2013.01); *A61B 6/465* (2013.01); *G06F 19/321* (2013.01); *G06F 19/3406* (2013.01)

(58) Field of Classification Search
USPC ......... 715/705, 709, 719, 715, 723, 763, 764, 715/777, 778
See application file for complete search history.

(56) References Cited

U.S. PATENT DOCUMENTS

| | | | |
|---|---|---|---|
| 2009/0274384 A1* | 11/2009 | Jakobovits | 382/254 |
| 2010/0274120 A1* | 10/2010 | Heuscher | 600/424 |
| 2012/0310668 A1* | 12/2012 | Kotula et al. | 705/3 |

* cited by examiner

*Primary Examiner* — Weilun Lo
*Assistant Examiner* — Truc Chuong
(74) *Attorney, Agent, or Firm* — Ziolkowski Patent Solutions Group, SC

(57) ABSTRACT

A user interface configured to display a first set of subject data in a first image workspace on the at least one display. The user interface is further configured to provide for user selection of at least one of a plurality of subject data related to a plurality of image workspaces, attach user comments to and save user comments with the user-selected subject data in the first user-selectable tab after input of user comments, electronically mail the user-selected subject data to one or more designated recipients directly from a first user-selectable tab after input of instructions to electronically mail the user-selected subject data, and automatically open a second image workspace related to the user-selected subject data after user selection of a return link in the first user-selectable tab.

20 Claims, 2 Drawing Sheets

USER INTERFACE FOR MEDICAL IMAGING SYSTEM APPLICATIONS

BACKGROUND OF THE INVENTION

Embodiments of the invention relate generally an operator-interactive computer system interfaced with a medical imaging apparatus. The medical imaging apparatus is capable of scanning a patient and thereafter producing a digital image of a region of interest (ROI) within the patient. The operator-interactive computer system is capable of enabling an operator to capture, display, and manipulate each digital image for medical diagnosis and clinical research purposes.

In a modern healthcare setting, multiple medical imaging apparatus systems are commonly networked to a central image management system. The medical imaging apparatuses themselves commonly utilize, for example, electromagnetic radiation, x-rays, sonic waves, or photonic energy to produce viewable digital images of internal regions within a subject of interest. Once produced, these digital images may then be utilized by a medical professional to aid in the examination, diagnosis, and/or treatment of the patient. Frequently, one particular type of medical imaging apparatus is preferable over another type of apparatus for producing digital images of a certain ROI within a patient. For example, ultrasound imaging apparatuses are particularly useful for producing digital images of a fetus during prenatal care, whereas magnetic resonance (MR) imaging apparatuses are useful for producing digital images of a wide range of tissues within a patient for the detection of potentially cancerous lesions.

The central image management system typically includes a central storage unit that is coupled to a plurality of operator-interactive workstations. The central storage unit itself is particularly configured to store or archive digital images produced by any of the medical imaging apparatus systems networked thereto. In addition, the central storage unit is also configured to allow the selective retrieval of digital images therefrom for display on any of the workstations networked to or within the central image management system. In this way, if the facility has a large number of medical imaging apparatuses situated throughout, digital images produced by any one or more of the medical imaging apparatus systems can be selectively stored or archived in the central storage unit and then later selectively retrieved and viewed by one or more medical professionals working at any one or more of the workstations.

When a medical professional, as an operator, conducts work on a workstation, the operator is able to selectively retrieve and view digital images from one or more sets of archived images produced during one or more prior examinations of a particular patient. In addition to viewing digital images, other information such as medical imaging apparatus identification, imaging parameters, presiding physician identification, and identifying information associated with the patient are all accessible and viewable, as well. Once an operator selects and successfully displays a digital image on the monitor screen of a workstation, the operator is then able to manipulate the image such as by zooming in on a portion of the image or by changing the viewing order of the image within a set of images. The operator can also selectively move and store sets of images in different categories of computer work files. In order to facilitate an operator's successful and expedited navigation through and between digital image sets and computer work files, the workstation includes a user-friendly graphical user interface (GUI) on the screen of its monitor. The GUI is typically designed such that the operator can specify his or her on-screen viewing preferences relating to the visual layout of the on-screen icons displayed by the GUI.

Although there are numerous different types of medical imaging apparatuses, some of the more prevalent types include computed tomography (CT) imaging apparatuses, magnetic resonance (MR) imaging apparatuses, ultrasound imaging apparatuses, and x-ray imaging apparatuses. As alluded to earlier herein, although each medical imaging modality functions and operates in a manner different from the other types, all types generally operate to focus on at least one ROI within the patient and produce digital images of those regions. In this way, once the digital images are produced, the digital images may then be utilized by medical professionals to aid in the examination, diagnosis, and treatment of patients.

An example of a specific implementation of these various medical imaging modalities is the use of computed tomography (CT) in cardiac imaging. As described above, a medical professional using one workstation can perform cardiac imaging on a patient utilizing CT. Thereafter, one or more medical professionals (e.g., a cardiologist) may access the captured digital images from other workstations in the network. From any of these workstations, the medical professional(s) may use the workstation GUI to view a plurality of indexed images acquired during cardiac imaging, including all manipulations and annotations made with regard to the image.

Unfortunately, however, conventional workstations and workstation GUIs do not enable the medical professional to have streamlined access to the specific workspace from which the digital image they are viewing was taken. Furthermore, conventional workstations and workstation GUIs do not provide the user with a simplified option for electronically mailing selected digital images to desired recipients. Currently, a user must save desired digital images to a USB device, CD, DVD, or other electronic storage device, upload the digital images from the storage device to a personal computer, and then electronically mail the uploaded digital images from the personal computer. Additionally, current workstation GUIs do not enable a user to make substantial comments related to the digital image, wherein these comments are stored and displayed with the image, but not located on the image itself. Conventional annotation of images is provided on the image itself and typically comprises only a brief label of anatomy or pathology. Such annotations, however, obstruct portions of the image, and thus user comments should be limited so as not to obstruct diagnostically important portions of the image.

Therefore, it would be desirable to provide a medical imaging device having a user interface capable of enabling simplified user access to the original workspace of a given digital image, direct electronic mailing of selected digital images, and increased image annotation capabilities, wherein these user comments are automatically associated with, and saved with, the selected digital image.

BRIEF DESCRIPTION OF THE INVENTION

An embodiment of the invention is directed to an apparatus comprising an imaging system configured to acquire image data of a subject, the imaging system comprising a user interface having at least one display, and a central image management system operably linked to the imaging system such that the user interface is in communication with the central image management system to allow for bi-directional data transfer therebetween. The user interface is configured to access the central image management system to retrieve subject data stored in the central image management system, display a first set of subject data in a first image workspace on the at least one display, wherein the first image workspace comprises a plurality of user-selectable tabs thereon, and provide for user selection of a first user-selectable tab, wherein the first user-selectable tab is configured to display a plurality of subject data related to a plurality of image workspaces in a separate display pane superimposed upon the first image workspace. The user interface is further configured to provide for user selection of at least one of the plurality of subject data related to the plurality of image workspaces, attach user comments to and save user comments with the user-selected subject data in the first user-selectable tab after input of user comments, electronically mail the user-selected subject data to one or more designated recipients directly from the first user-selectable tab after input of instructions to electronically mail the user-selected subject data, and automatically open a second image workspace related to the user-selected subject data after user selection of a return link in the first user-selectable tab.

Another embodiment of the invention is directed to a method for diagnostic imaging implementing an imaging system that includes a user interface, the method comprising accessing a central image management system to retrieve patient data stored in the central image management system, displaying a first set of patient data in a first image workspace on a display monitor, wherein the first image workspace comprises a plurality of user-selectable tabs thereon, and displaying, in a first user-selected tab, a plurality of images related to a plurality of image workspaces in a separate display pane superimposed upon the first image workspace. The method further comprises providing for user selection of at least one of the plurality of images related to the plurality of image workspaces, attaching user comments to saving user comments with the at least one user-selected image displayed in the first user-selectable tab, electronically mailing the at least one user-selected image to one or more designated recipients directly from the first user-selectable tab after user input of instructions to electronically mail the user-selected image, and opening a second image workspace pertaining to the at least one user-selected image from the first user-selectable tab after user selection of a return link in the first user-selectable tab.

Another embodiment of the invention is directed to a digital imaging apparatus comprising a user-accessible workstation comprising at least one display and a graphical user interface. The graphical user interface is configured to be viewable on the at least one display, wherein the graphical user interface is further configured to display a user-selected image workspace on the at least one display, wherein the user-selected image workspace comprises an image depicting a region of interest of a subject and a plurality of user-selectable tabs thereon, provide for user selection of a first user-selectable tab, wherein the first user-selectable tab is configured to display a plurality of images related to a plurality of image workspaces in a separate display pane superimposed upon the user-selected image workspace, and provide for user selection of one of the plurality of images. The graphical user interface is further configured to attach user comments to and save user comments with the user-selected image directly from the first user-selectable tab, electronically mail the user-selected image to one or more designated recipients directly from the first user-selectable tab, and open another image workspace related to the user-selected image from the first user-selectable tab after user selection of a return link in the first user-selectable tab.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a computed tomography (CT) system. However, it will be appreciated by those skilled in the art that the invention is equally applicable for use with other imaging modalities, such as magnetic resonance (MR) imaging systems, ultrasound imaging systems, x-ray systems, etc.

Figure 1:
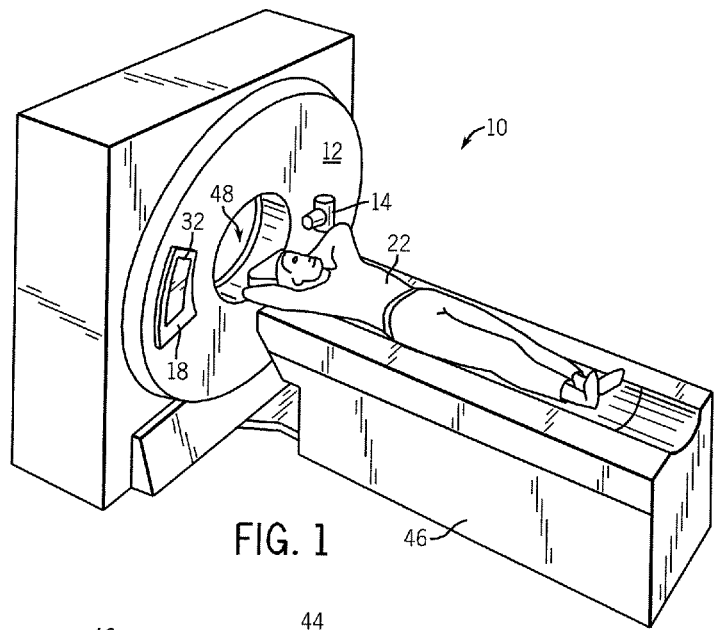
FIG. 1 is a pictorial view of a CT imaging system.
Figure 2:
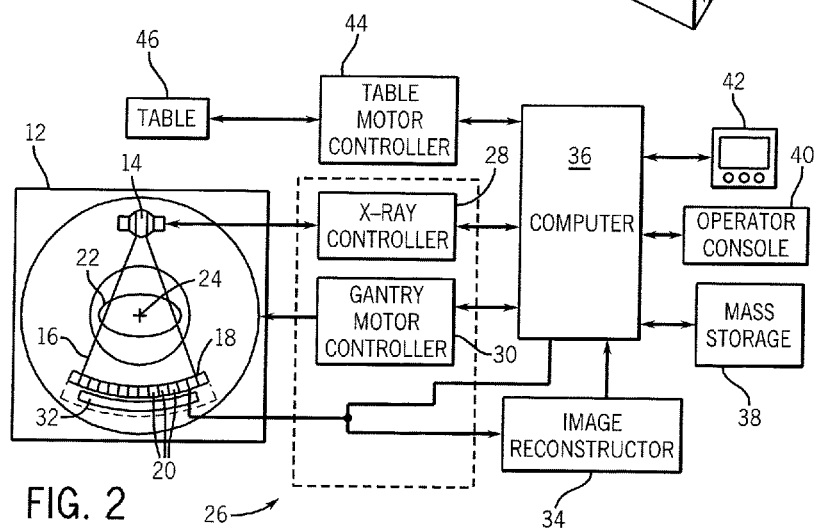
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

While FIG. 2 illustrates only a single computer 36 coupled to mass storage device 38, it is to be understood that a plurality of computer workstations may be configured to remotely access mass storage device 38 to view the reconstructed images stored therein. Each of these computer workstations may similarly comprise a console 40 having an operator interface, as well as a display 42 to allow the remote operator to observe the reconstructed image of a region of interest (ROI) of the patient and other data stored in mass storage device 38. In this way, an operator (e.g., a medical professional) may view and manipulate reconstructed images captured via CT imaging system 10 from any computer workstation coupled to mass storage device 38.

Figure 3:
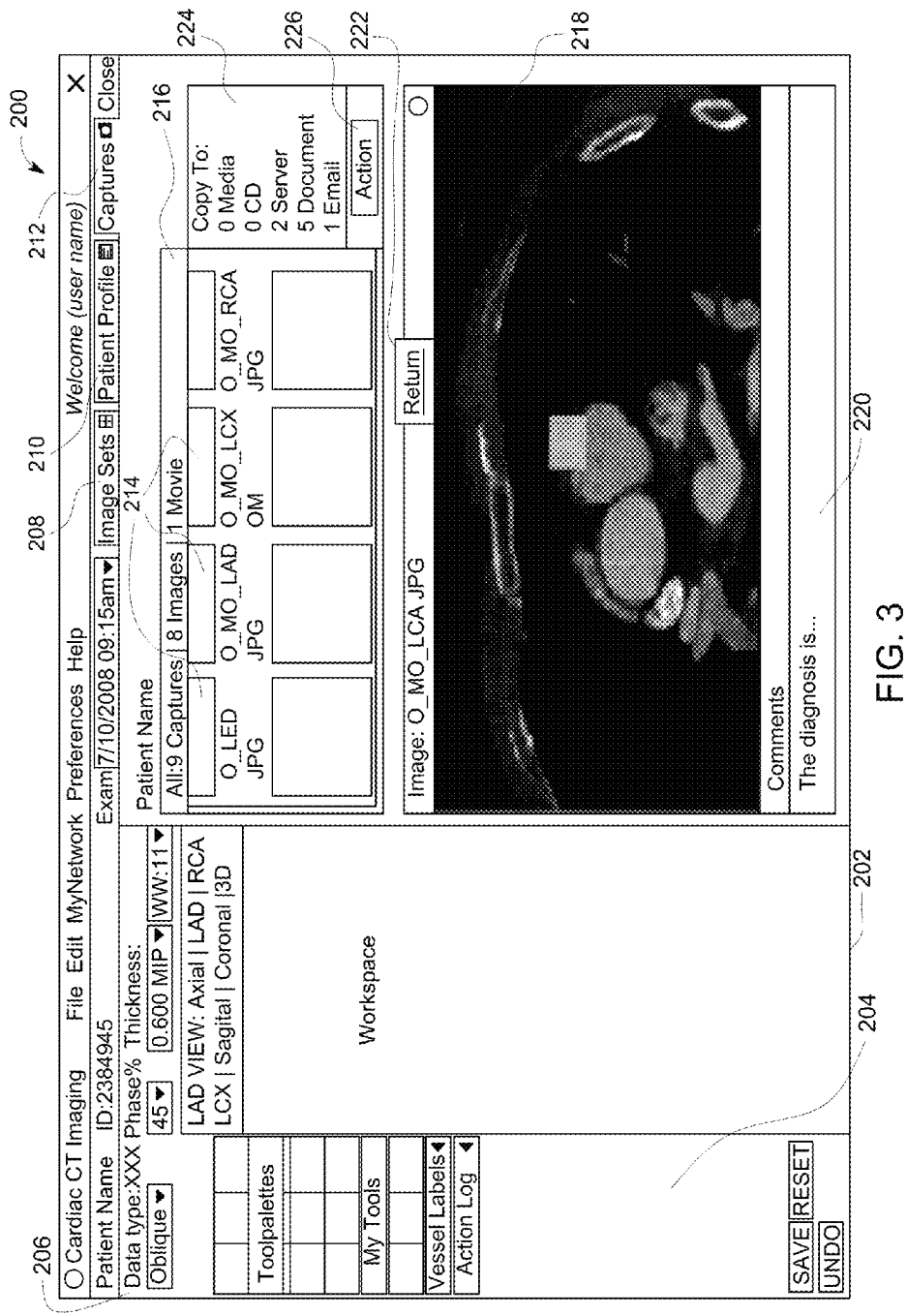
FIG. 3 is a screen view of a graphical user interface in accordance with an embodiment of the invention.

Referring now to FIG. 3, a screenshot of a graphical user interface 200 in accordance with an embodiment of the invention is shown. Graphical user interface 200 is configured to be shown on display 42 of any appropriate computer workstation having access to mass storage device 38. For a given patient or subject, graphical user interface 200 displays a reconstructed image or images related to a specific ROI in a workspace pane 202, along with a workspace toolbar 204 and an image data information bar 206. Graphical user interface 200 further comprises tabs 208, 210, and 212, which the operator is capable of individually selecting via an operator interface (such as operator interface 40 described with respect to FIG. 2). In FIG. 3, tab 208 comprises image sets, tab 210 comprises patient profile information, and tab 212, entitled "Captures", comprises a plurality of user-selectable features regarding captured reconstructed images, as will be described further herein. While tabs 208, 210, and 212 are shown, it is to be understood that the invention is not limited solely to such a tab configuration having these specific features, as more or fewer tabs may be implemented.

When the operator has completed viewing and/or manipulating an image displayed in workspace pane 202, the operator may save the image via workspace toolbar 204, at which point the image is automatically saved to "Captures" tab 212. The operator may select tab 212, which opens a separate display pane that is superimposed over workspace pane 202. Selected tab 212 includes a plurality of thumbnail images 214 displayed in an image repository 216, wherein thumbnail images 214 each relate to a saved reconstructed image of a particular ROI of the patient.

Upon operator selection of one of the plurality of thumbnail images 214, tab 212 is further configured to display a preview pane 218 related to the selected thumbnail image 214. Preview pane 218 includes an enlarged view of the selected thumbnail image 214, along with a text box 220 located adjacent to the enlarged view of the selected thumbnail image 214. Text box 220 enables the operator to input substantial comments and observations regarding the selected image without the concern for character limitations typically associated with annotations made regarding diagnostic images. Furthermore, as text box 220 is located adjacent to the selected image, the operator does not need to be concerned that the comments entered into text box 220 will interfere with the view of the selected image shown in preview pane 218 in any way. Additionally, the comments entered into text box 220 are automatically saved with the selected image, thereby enabling the operator to continuously update and revise the comments as needed and/or view comments entered by another operator with respect to the selected image. The ability to add comments in text box 220 in this way greatly benefits the operator's efficiency and effectiveness in incorporating operator thoughts and diagnostic opinions with regard to the selected image.

Referring still to FIG. 3, preview pane 218 of tab 212 further comprises a return link 222 thereon. When selected by the operator via an operator interface, return link 222 is configured to open (within workspace pane 202) the original workspace from which the selected image displayed in preview pane 218 was captured and saved. This feature enables the operator to further manipulate and view the selected image in its original workspace environment, and eliminates the previous need for the user to close the program and retrace steps to return to the original workspace of the image, thereby improving the overall efficiency of the operator's workflow. While return link 222 is shown in FIG. 3 as being located on a top portion of preview pane 218, the invention is not limited as such, and return link 222 may be located anywhere within tab 212.

Graphical user interface 200 shown in FIG. 3 further includes an action menu 224. The operator may select one or more of the plurality of thumbnail images 214 from image repository 216 and drag-and-drop the one or more thumbnail images 214 to a preferred destination within action menu 224. For example, if the operator wishes to electronically mail one or more of the images related to thumbnail images 214, the operator may select the desired thumbnail image(s) 214 and drag-and-drop the image over the "email" action listed in action menu 224. When at least one thumbnail image 214 is copied to the "email" action, action link 226, labeled as "Action" in FIG. 3, is re-labeled to read "Send". When the operator has chosen all desired thumbnail images 214 for transmission, the operator may select action link 226 labeled "Send". The selected image(s) are then either automatically sent to previously-designated recipients or the operator's electronic mail package is accessed, with the images related to selected thumbnail images 214 attached to a new electronic message, thereby allowing the operator to conveniently send the images to any desired recipients through a conventional electronic mail package or program. In this way, the operator is able to send selected images to one or more designated recipients without the need to exit the workspace, thereby greatly improving the efficiency and accuracy of electronic mail communications as compared with previous methods.

As mentioned above, while embodiments of the invention have been described with respect to a computed tomography (CT) system, the embodiments are equally applicable for use with other imaging modalities, such as magnetic resonance (MR) imaging systems, ultrasound imaging systems, x-ray systems, etc. The invention is also quite useful in specific applications of these imaging modalities, such as cardiac CT imaging and analysis, as it allows the cardiologist or other medical professional to actively and efficiently view, annotate, and share important images and image data from one convenient location in their workflow.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

Accordingly, an embodiment of the invention is directed to an apparatus comprising an imaging system configured to acquire image data of a subject, the imaging system comprising a user interface having at least one display, and a central image management system operably linked to the imaging system such that the user interface is in communication with the central image management system to allow for bi-directional data transfer therebetween. The user interface is configured to access the central image management system to retrieve subject data stored in the central image management system, display a first set of subject data in a first image workspace on the at least one display, wherein the first image workspace comprises a plurality of user-selectable tabs thereon, and provide for user selection of a first user-selectable tab, wherein the first user-selectable tab is configured to display a plurality of subject data related to a plurality of image workspaces in a separate display pane superimposed upon the first image workspace. The user interface is further configured to provide for user selection of at least one of the plurality of subject data related to the plurality of image workspaces, attach user comments to and save user comments with the user-selected subject data in the first user-selectable tab after input of user comments, electronically mail the user-selected subject data to one or more designated recipients directly from the first user-selectable tab after input of instructions to electronically mail the user-selected subject data, and automatically open a second image workspace related to the user-selected subject data after user selection of a return link in the first user-selectable tab.

Another embodiment of the invention is directed to a method for diagnostic imaging implementing an imaging system that includes a user interface, the method comprising accessing a central image management system to retrieve patient data stored in the central image management system, displaying a first set of patient data in a first image workspace on a display monitor, wherein the first image workspace comprises a plurality of user-selectable tabs thereon, and displaying, in a first user-selected tab, a plurality of images related to a plurality of image workspaces in a separate display pane superimposed upon the first image workspace. The method further comprises providing for user selection of at least one of the plurality of images related to the plurality of image workspaces, attaching user comments to saving user comments with the at least one user-selected image displayed in the first user-selectable tab, electronically mailing the at least one user-selected image to one or more designated recipients directly from the first user-selectable tab after user input of instructions to electronically mail the user-selected image, and opening a second image workspace pertaining to the at least one user-selected image from the first user-selectable tab after user selection of a return link in the first user-selectable tab.

Another embodiment of the invention is directed to a digital imaging apparatus comprising a user-accessible workstation comprising at least one display and a graphical user interface. The graphical user interface is configured to be viewable on the at least one display, wherein the graphical user interface is further configured to display a user-selected image workspace on the at least one display, wherein the user-selected image workspace comprises an image depicting a region of interest of a subject and a plurality of user-selectable tabs thereon, provide for user selection of a first user-selectable tab, wherein the first user-selectable tab is configured to display a plurality of images related to a plurality of image workspaces in a separate display pane superimposed upon the user-selected image workspace, and provide for user selection of one of the plurality of images. The graphical user interface is further configured to attach user comments to and save user comments with the user-selected image directly from the first user-selectable tab, electronically mail the user-selected image to one or more designated recipients directly from the first user-selectable tab, and open another image workspace related to the user-selected image from the first user-selectable tab after user selection of a return link in the first user-selectable tab.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus comprising:
   an imaging system configured to acquire image data of a subject, the imaging system comprising a user interface having at least one display;
   a central image management system operably linked to the imaging system such that the user interface is in communication with the central image management system to allow for bi-directional data transfer therebetween; and
   wherein the user interface is configured to:
      access the central image management system to retrieve subject data stored in the central image management system;
      display a first set of subject data in a first image workspace on the at least one display, wherein the first image workspace comprises a plurality of user-selectable tabs thereon;
      provide for user selection of a first user-selectable tab, wherein the first user-selectable tab is configured to display a plurality of subject data related to a plurality of image workspaces in a separate display pane superimposed upon the first image workspace;
      provide for user selection of at least one of the plurality of subject data related to the plurality of image workspaces;
      attach user comments to and save user comments with the user-selected subject data in the first user-selectable tab after input of user comments;
      electronically mail the user-selected subject data to one or more designated recipients directly from the first user-selectable tab after input of instructions to electronically mail the user-selected subject data; and
      automatically open a second image workspace related to the user-selected subject data after user selection of a return link in the first user-selectable tab.

2. The apparatus of claim 1 wherein the displayed plurality of subject data related to a plurality of image workspaces comprises a display of a plurality of thumbnail images related to the subject data.

3. The apparatus of claim 1 wherein the user interface is further configured to display an image of the user-selected subject data within the separate display pane superimposed upon the first image workspace.

4. The apparatus of claim 3 wherein the user interface is further configured to open the second image workspace of the user-selected subject data via a return link provided on the displayed image of the user-selected subject data.

5. The apparatus of claim 3 wherein the user interface is further configured to display the user comments in a window adjacent to the image of the user-selected subject data.

6. The apparatus of claim 4 wherein the user interface is further configured to allow the user to update the user comments.

7. The apparatus of claim 1 wherein the user interface is further configured to allow the user to drag-and-drop at least one image representing the user-selected subject data to an electronic mail folder in the separate display pane prior to sending the at least one image to the one or more designated recipients.

8. The apparatus of claim 7 wherein the user interface is further configured to generate an electronic mail link in the separate display pane when the user completes the drag-and-drop of at least one image to the electronic mail folder so as to enable automatic dispersal of the at least one image to the one or more designated recipients.

9. The apparatus of claim 1 wherein the imaging system comprises one of a computed tomography (CT) imaging apparatus, a magnetic resonance (MR) imaging apparatus, an ultrasound imaging apparatus, and an x-ray imaging apparatus.

10. The apparatus of claim 9 wherein the imaging system comprises a CT imaging apparatus utilized for cardiac radiology.

11. A method for diagnostic imaging implementing an imaging system that includes a user interface, the method comprising:
accessing a central image management system to retrieve patient data stored in the central image management system;
displaying a first set of patient data in a first image workspace on a display monitor, wherein the first image workspace comprises a plurality of user-selectable tabs thereon;
displaying, in a first user-selected tab, a plurality of images related to a plurality of image workspaces in a separate display pane superimposed upon the first image workspace;
providing for user selection of at least one of the plurality of images related to the plurality of image workspaces;
attaching user comments to saving user comments with the at least one user-selected image displayed in the first user-selectable tab;
electronically mailing the at least one user-selected image to one or more designated recipients directly from the first user-selectable tab after user input of instructions to electronically mail the user-selected image; and
opening a second image workspace pertaining to the at least one user-selected image from the first user-selectable tab after user selection of a return link in the first user-selectable tab.

12. The method of claim 11 further comprising returning to an original image workspace of the user-selected image after user selection of a link provided on the displayed image in the first user-selectable tab.

13. The method of claim 11 further comprising displaying the user comments with the user-selected image displayed in the first user-selectable tab.

14. The method of claim 11 further comprising updating the user comments when viewing the user-selected image displayed in the first user-selectable tab.

15. The method of claim 11 further comprising dragging-and-dropping the at least one user-selected image to an electronic mail folder in the separate display pane prior to sending the at least one user-selected image to the one or more designated recipients.

16. A digital imaging apparatus comprising:
a user-accessible workstation comprising at least one display; and
a graphical user interface configured to be viewable on the at least one display, wherein the graphical user interface is further configured to:
display a user-selected image workspace on the at least one display, wherein the user-selected image workspace comprises an image depicting a region of interest of a subject and a plurality of user-selectable tabs thereon;
provide for user selection of a first user-selectable tab, wherein the first user-selectable tab is configured to display a plurality of images related to a plurality of image workspaces in a separate display pane superimposed upon the user-selected image workspace;
provide for user selection of one of the plurality of images;
attach user comments to and save user comments with the user-selected image directly from the first user-selectable tab;
electronically mail the user-selected image to one or more designated recipients directly from the first user-selectable tab; and
open another image workspace related to the user-selected image from the first user-selectable tab after user selection of a return link in the first user-selectable tab.

17. The digital imaging apparatus of claim 16 wherein the graphical user interface further comprises a link provided on the user-selected image to return to the image workspace of the user-selected image.

18. The digital imaging apparatus of claim 16 wherein the graphical user interface is further configured to display the user comments with the user-selected image in the first user-selectable tab.

19. The digital imaging apparatus of claim 16 wherein the graphical user interface is further configured to allow the user to drag-and-drop the user-selected image to an electronic mail folder in the separate display pane prior to sending the user-selected image to the one or more designated recipients.

20. The digital imaging apparatus of claim 16 wherein the digital imaging apparatus is one of a computed tomography (CT) imaging apparatus, a magnetic resonance (MR) imaging apparatus, an ultrasound imaging apparatus, and an x-ray imaging apparatus.

* * * * *